United States Patent
Singh et al.

(10) Patent No.: US 9,878,721 B2
(45) Date of Patent: Jan. 30, 2018

(54) TIRE SENSOR-BASED ROBUST MILEAGE TRACKING SYSTEM AND METHOD

(71) Applicant: The Goodyear Tire & Rubber Company, Akron, OH (US)

(72) Inventors: Kanwar Bharat Singh, Stow, OH (US); Peter Jung-min Suh, Copley, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 14/938,181

(22) Filed: Nov. 11, 2015

(65) Prior Publication Data

US 2017/0129498 A1 May 11, 2017

(51) Int. Cl.
| | | |
|---|---|---|
| G01M 17/00 | (2006.01) | |
| G06F 7/00 | (2006.01) | |
| G06F 19/00 | (2011.01) | |
| B60W 40/105 | (2012.01) | |
| B60C 23/00 | (2006.01) | |
| G01M 17/02 | (2006.01) | |
| G01N 3/56 | (2006.01) | |
| B60C 11/24 | (2006.01) | |
| B60C 23/04 | (2006.01) | |
| G07C 5/08 | (2006.01) | |

(52) U.S. Cl.
CPC .......... *B60W 40/105* (2013.01); *B60C 11/243* (2013.01); *B60C 11/246* (2013.01); *B60C 23/00* (2013.01); *B60C 23/04* (2013.01); *B60C 23/0408* (2013.01); *B60C 23/0486* (2013.01); *G01M 17/02* (2013.01); *G01N 3/56* (2013.01); *G07C 5/0816* (2013.01)

(58) Field of Classification Search
CPC .......... B60C 23/00; G01M 17/02; G01N 3/56
USPC ....................................................... 701/29.1
See application file for complete search history.

(56) References Cited

U.S. PATENT DOCUMENTS

| | | | |
|---|---|---|---|
| 7,483,794 B2 | 1/2009 | Bocquillon | |
| 8,661,885 B1 * | 3/2014 | Singh .................. | B60C 23/0408 701/1 |
| 9,050,864 B2 | 6/2015 | Singh et al. | |
| 2008/0278304 A1 | 11/2008 | Klesewetter et al. | |
| 2014/0107946 A1 | 4/2014 | Kandler et al. | |
| 2015/0040656 A1 | 2/2015 | Singh et al. | |

FOREIGN PATENT DOCUMENTS

KR         2008053975 A  *  6/2008

OTHER PUBLICATIONS

EPO Search Report received by Applicant dated Mar. 31, 2017.

* cited by examiner

*Primary Examiner* — Maceeh Anwari
(74) *Attorney, Agent, or Firm* — Edward T. Kennedy

(57) ABSTRACT

A tire tracking system and method for tracking travel mileage experienced by a vehicle tire includes multiple tire-based sensors affixed to the tire generating identified tire-specific operating condition measurements. The tire-specific operating condition measurements include tire temperature, tire air inflation pressure, a tire wear state measurement and a tire load measurement. A rolling radius estimation model generates a tire rolling radius estimation compensated by the tire-specific operating condition measurements and a vehicle speed estimator generates a vehicle speed estimation based on the compensated tire rolling radius.

12 Claims, 7 Drawing Sheets

Rolling Radius Analysis Sensitivities – Summary

| | Effect on Rolling Radius | Sensitively |
|---|---|---|
| Increasing Load | Decreases | 1mm/300lbs |
| Increasing Pressure | Increases | 0.5mm/4psi |
| Decreasing Tread Depth | Decreases | 0.3mm/3mm |

TIRE SENSOR-BASED ROBUST MILEAGE TRACKING SYSTEM AND METHOD

FIELD OF THE INVENTION

The invention relates generally to tire monitoring systems for determining mileage on a tire and, more particularly, to systems utilizing tire rolling radius to calculate vehicle speed and vehicle distance traveled.

BACKGROUND OF THE INVENTION

Tire mileage calculation for determining mileage history on a tire is calculated from the distance driven by the vehicle carried by the tire. Vehicle distance traveled can be determined from GPS data but such data can be unreliable. Vehicle speed may also be calculated from information based on CAN-bus wheel speed signals over a time interval used in conjunction with tire rolling radius. Determination of tire rolling radius for use in such calculations can, however, be error prone. Error in rolling radius used in the calculations can lead to error in the speed calculation and, consequently, the tire mileage calculations. There is, accordingly, a need for a tire mileage tracking system that is based on a robust, accurate, and reliable determination of tire rolling radius for use in calculating vehicle speed and distance traveled.

SUMMARY OF THE INVENTION

In one aspect of the invention, a tire tracking system and method for tracking travel mileage experienced by a vehicle tire includes multiple tire-based sensors affixed to the tire generating identified tire-specific operating condition measurements. The tire-specific operating condition measurements include tire temperature, tire air inflation pressure, a tire wear state measurement and a tire load measurement. A rolling radius estimation model generates a tire rolling radius estimation compensated by the tire-specific operating condition measurements and a vehicle speed estimator generates a vehicle speed estimation based on the compensated tire rolling radius.

In another aspect of the invention, included within the tire-based sensors is a tire-affixed identification transponder generating tire-specific identification data used in generating the tire load estimation.

According to a further aspect, a vehicle-mounted sensor generates a CAN-bus accessible wheel speed measurement for the tire used in making the vehicle speed estimation.

Definitions

"ANN" or "Artificial Neural Network" is an adaptive tool for non-linear statistical data modeling that changes its structure based on external or internal information that flows through a network during a learning phase. ANN neural networks are non-linear statistical data modeling tools used to model complex relationships between inputs and outputs or to find patterns in data.

"Aspect ratio" of the tire means the ratio of its section height (SH) to its section width (SW) multiplied by 100 percent for expression as a percentage.

"Asymmetric tread" means a tread that has a tread pattern not symmetrical about the center plane or equatorial plane EP of the tire.

"Axial" and "axially" means lines or directions that are parallel to the axis of rotation of the tire.

"Chafer" is a narrow strip of material placed around the outside of a tire bead to protect the cord plies from wearing and cutting against the rim and distribute the flexing above the rim.

"Circumferential" means lines or directions extending along the perimeter of the surface of the annular tread perpendicular to the axial direction.

"Dugoff Model" is an empirical tire model providing analytical relations for the longitudinal and lateral forces as functions of the slip angle and slip ratio. It accounts for the coupling between the side and longitudinal forces.

"Equatorial Centerplane (CP)" means the plane perpendicular to the tire's axis of rotation and passing through the center of the tread.

"Footprint" means the contact patch or area of contact created by the tire tread with a flat surface as the tire rotates or rolls.

"Groove" means an elongated void area in a tire wall that may extend circumferentially or laterally about the tire wall. The "groove width" is equal to its average width over its length. A grooves is sized to accommodate an air tube as described.

"Inboard side" means the side of the tire nearest the vehicle when the tire is mounted on a wheel and the wheel is mounted on the vehicle.

"Lateral" means an axial direction.

"Lateral edges" means a line tangent to the axially outermost tread contact patch or footprint as measured under normal load and tire inflation, the lines being parallel to the equatorial centerplane.

"Net contact area" means the total area of ground contacting tread elements between the lateral edges around the entire circumference of the tread divided by the gross area of the entire tread between the lateral edges.

"Non-directional tread" means a tread that has no preferred direction of forward travel and is not required to be positioned on a vehicle in a specific wheel position or positions to ensure that the tread pattern is aligned with the preferred direction of travel. Conversely, a directional tread pattern has a preferred direction of travel requiring specific wheel positioning.

"Outboard side" means the side of the tire farthest away from the vehicle when the tire is mounted on a wheel and the wheel is mounted on the vehicle.

"Peristaltic" means operating by means of wave-like contractions that propel contained matter, such as air, along tubular pathways.

"Piezoelectric Film Sensor" a device in the form of a film body that uses the piezoelectric effect actuated by a bending of the film body to measure pressure, acceleration, strain or force by converting them to an electrical charge.

"Radial" and "radially" means directions radially toward or away from the axis of rotation of the tire.

"Rib" means a circumferentially extending strip of rubber on the tread which is defined by at least one circumferential groove and either a second such groove or a lateral edge, the strip being laterally undivided by full-depth grooves.

"Sipe" means small slots molded into the tread elements of the tire that subdivide the tread surface and improve traction, sipes are generally narrow in width and close in the tires footprint as opposed to grooves that remain open in the tire's footprint.

"Tread element" or "traction element" means a rib or a block element defined by having a shape adjacent grooves.

"Tread Arc Width" means the arc length of the tread as measured between the lateral edges of the tread.

BRIEF DESCRIPTION OF THE DRAWINGS

The invention will be described by way of example and with reference to the accompanying drawings in which:

FIG. 7 is a table summarizing load, pressure and tire wear effects on rolling radius.

DETAILED DESCRIPTION OF THE INVENTION

Figure 1:
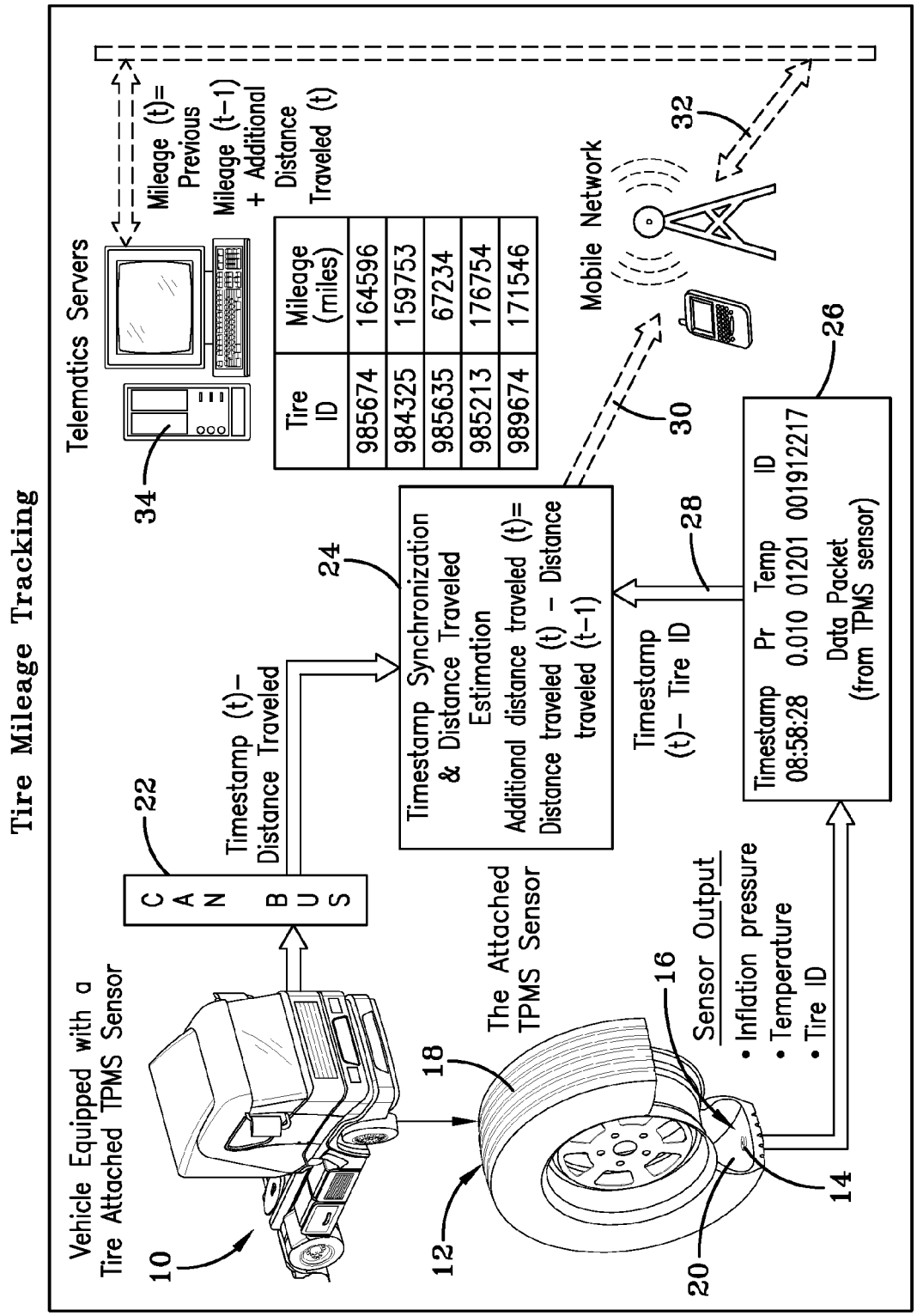
FIG. 1 is schematic of the prior art tire mileage tracking system and method.

Referring to FIG. 1, a system for tracking tire mileage is shown. The FIG. 1 system determines distance traveled from GPS or CAN-b signals and applies a tire identification code (tire ID) from a tire tag mounted to a vehicle tire. In the FIG. 1 system, a vehicle 10 is equipped with pneumatic tires 12. While vehicle 10 is seen as a commercial truck, other vehicle types are compatible with the use of the subject method and system. The tires 12 have respective dates of service implementation that may or may not coincide. Each tire 12 may accordingly have been placed into service at a different respective time. It is an objective of the prior art system and method to monitor and track each tire 12 individually in order to record important historical information regarding each tire. Such information may include aggregate service mileage experienced by the tire, historical pressure data of the tire and/or historical temperature data of the tire. The information gathered and recorded may prove useful to monitor tire history and assist in determining when the tire needs replacement.

The tires 12 are of conventional pneumatic construction having a tread 18 and an air cavity 16. An inner liner 20 defines the cavity 16. A tire monitoring device 14 is affixed to the tire inner liner 20, hereinafter referred to as a "TPMS" sensor. The device 14 includes tire identification information by which each individual tire may be identified. The device 14 may further include a temperature sensor for monitoring the temperature of the tire and a tire pressure sensor for monitoring the air pressure within cavity 16. One or more transmitters are further included within the device 14 for wirelessly transmitting tire identification data, temperature data and pressure data. Collectively, the tire ID, temperature data and pressure data of the tire is referred herein as the "data packet" from the TPMS device 14.

The device 14 attaches to the tire inner liner 20 by suitable means such as an adhesive. The data packet from the TPMS device 14 is time stamped at time (t) as seen at block 26, wherein the pressure temperature and tire ID are recorded at a specific time (t). The time stamped data packet is input into a timestamp synchronization and distance traveled estimation 24. The vehicle 10, in the first embodiment of the system shown in FIG. 1, is equipped with one or more sensors measuring vehicle distance travelled and providing via CAN-bus 22 the measured vehicle distance travelled at timestamp (t). The vehicle distance travelled at timestamp (t) is input into the timestamp synchronization and distance travelled estimation 24. The timestamp synchronization and distance travelled estimation 24 takes the vehicle distance travelled at (t) since the last distance travelled at (t−1) and uploads the distance 30 to a mobile network 32. The distance travelled estimation is then uploaded via the mobile network 32 to a telematic server 34 with the data packet for the tire. The telematic server 34 maintains a record of mileage (t) equals previous for the tire, continuously updated by mileage (t−1) plus additional distance traveled (t). As seen in FIG. 1, recorded mileage for each tire is maintained and accessible by means of the tire ID received telemetrically from the vehicle 10. The service mileage for each tire, along with historical pressure and temperature data from the data packet for the tire is accordingly accessible to assist fleet operators in assessing the history of each tire on a vehicle. The data packet from the TPMS system with the additional distance travelled is sent at 30 to the telematic server 34 by means of a mobile network 32.

Estimates of vehicle speed solely based on GPS signals may not be as reliable (e.g. issues with GPS signal drop off etc.). Accordingly, vehicle speed information on the CAN-bus may be preferable. CAN-bus information is based off wheel speed signals and the tire rolling radius (vehicle speed=rolling radius×omega; where omega is the average of the four wheel speeds).

Vehicle speed is typically obtained from either GPS (global positioning system) or from vehicle CAN-bus information. GPS based estimates of vehicle speed are not very reliable (e.g. issues with GPS signal drop off, etc.). Vehicle speed information on the CAN-bus is based off of wheel speed signals and the tire rolling radius. Rolling radius of the tire, however, changes as a function of certain tire operating conditions such as load, pressure, wear state, tire construction characteristics, etc. These changes in vehicle operating conditions can cause an error in the speed calculations and consequently the tire mileage calculations.

Figure 2:
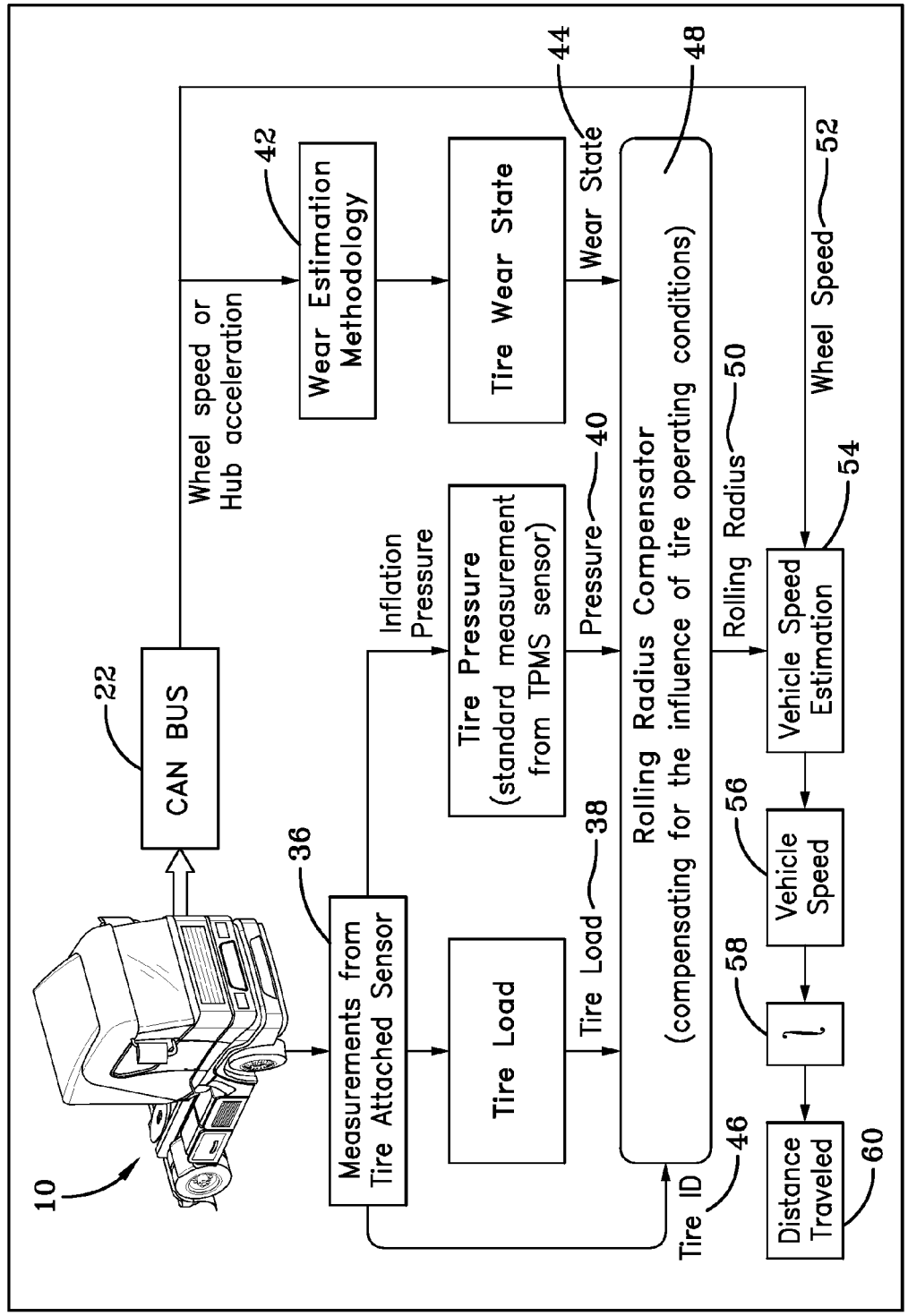
FIG. 2 is a schematic representation of improved vehicle speed estimation algorithm of the subject system and method.

Rolling radius of the tire is accordingly critical in the above algorithm for determining vehicle speed. The FIG. 1 system may use a database that gives the rolling radius of a tire as identified from the tire ID taken from a tire-attached tag. Typically, such information on rolling radius is based on a new tire in the unloaded condition. Alternatively, the algorithm in FIG. 2 may be employed to render a more predictably accurate vehicle speed estimation. In FIG. 2, a vehicle speed estimation algorithm is presented from which a robust, accurate and reliable determination of vehicle speed may be obtained.

Referring to FIG. 2, the improved vehicle speed estimation algorithm uses measurements 36 from a tire-affixed TPMS module. Such measurements are used to provide estimations of tire load 38, tire pressure 40 and wear estimation 42. In addition, vehicle-based sensors are employed to generate wheel speed or hub acceleration measurement. Such measurements are available via the vehicle CAN-bus 22.

Tire load 38 may be obtained from sensors mounted to the tire such as strain sensors. U.S. Pat. No. 8,661,885, issued Mar. 4, 2014, entitled TIRE SIDEWALL LOAD ESTIMATION SYSTEM AND METHOD discloses one such system and method for estimating tire load and is incorporated herein by reference in its entirety. The load estimation employed uses tire pressure, tire ID and tire temperature as inputs. Tire pressure and tire temperature are components of the tire operating condition packet that is retrieved from the TPMS module mounted to the tire. Inflation pressure 40 is measured directly from a pressure sensor component of the TPMS module affixed to each tire of the vehicle 10. Tire wear state 44 is obtained through the use of wear estimation methodology 42 such as those taught by U.S. Pat. No. 9,050,864 issued Jun. 9, 2015, entitled TIRE WEAR STATE ESTIMATION SYSTEM AND METHOD, or co-pending U.S. Patent Publication No. 2015/0040656, published Feb. 12, 2015, entitled TORSIONAL MODE TIRE WEAR STATE ESTIMATION SYSTEM AND METHOD, both of which incorporated herein by reference in their entireties.

An additional component of tire-based information in the subject system is the tire identification 46. Tire ID is obtained from a tag affixed to the tire either as a separate component or as part of the TPMS module attached to the tire. The tire ID 46 is the means by which the particular tire and its construction are identified. From that identification, in consultation with a database, tire-specific construction and relational correlations between tire pressure, temperature, wear state and load may be determined. In addition, the tire ID is used in U.S. Pat. No. 8,661,885 for the purpose of tire load estimation.

The wear estimation methodology 42 uses the wheel speed or hub acceleration measurements from the vehicle CAN-bus. Together, the tire load estimation 38, the pressure measurement 40 and the tire wear state estimation 44 are inputs with tire ID 46 into a rolling radius compensator 48 that compensates for the influence of tire inputted tire operating conditions. The compensator 48 combines the inputs and makes a database consultation for the particular combination of inputs to determine a compensated rolling radius 50. The tire ID makes the compensated rolling radius 50 tire-specific, that is, the rolling radius is adjusted based upon the inputs made for the particular tire construction indicated by the Tire ID.

The rolling radius 50 so compensated is then used to adjust wheel speed 52 from the CAN-bus 22 to generate a vehicle speed estimation 54. The vehicle speed 56 from the estimation 54 is subjected to time interval aggregation or integrated at 58 to yield a cumulative distance traveled 60 for the particular tire identified. That information may be uploaded to the vehicle memory and/or uploaded telemetrically to a remote tire-specific record.

Figure 3:
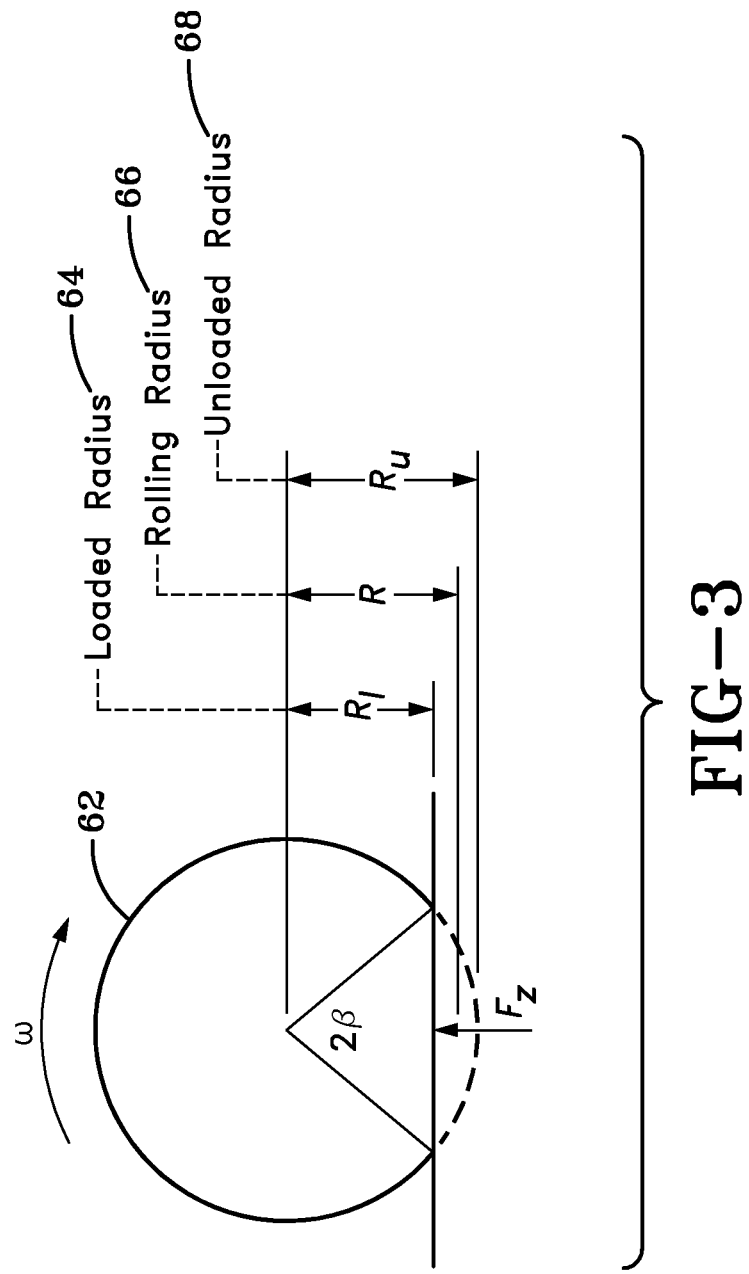
FIG. 3 is a diagram illustrating rolling radius sensitivity.

It will be understood how operating conditions such as loading for a tire effect rolling radius from the diagrammatic depiction of a tire 62 in FIG. 3. The unloaded radius 68 of a tire ($R_u$), the rolling radius (R) 66 and the loaded radius ($R_l$) 64 are shown. The effect of tire loading or unloading will be seen to have a significant impact on the rolling radius of the tire.

Figure 4:
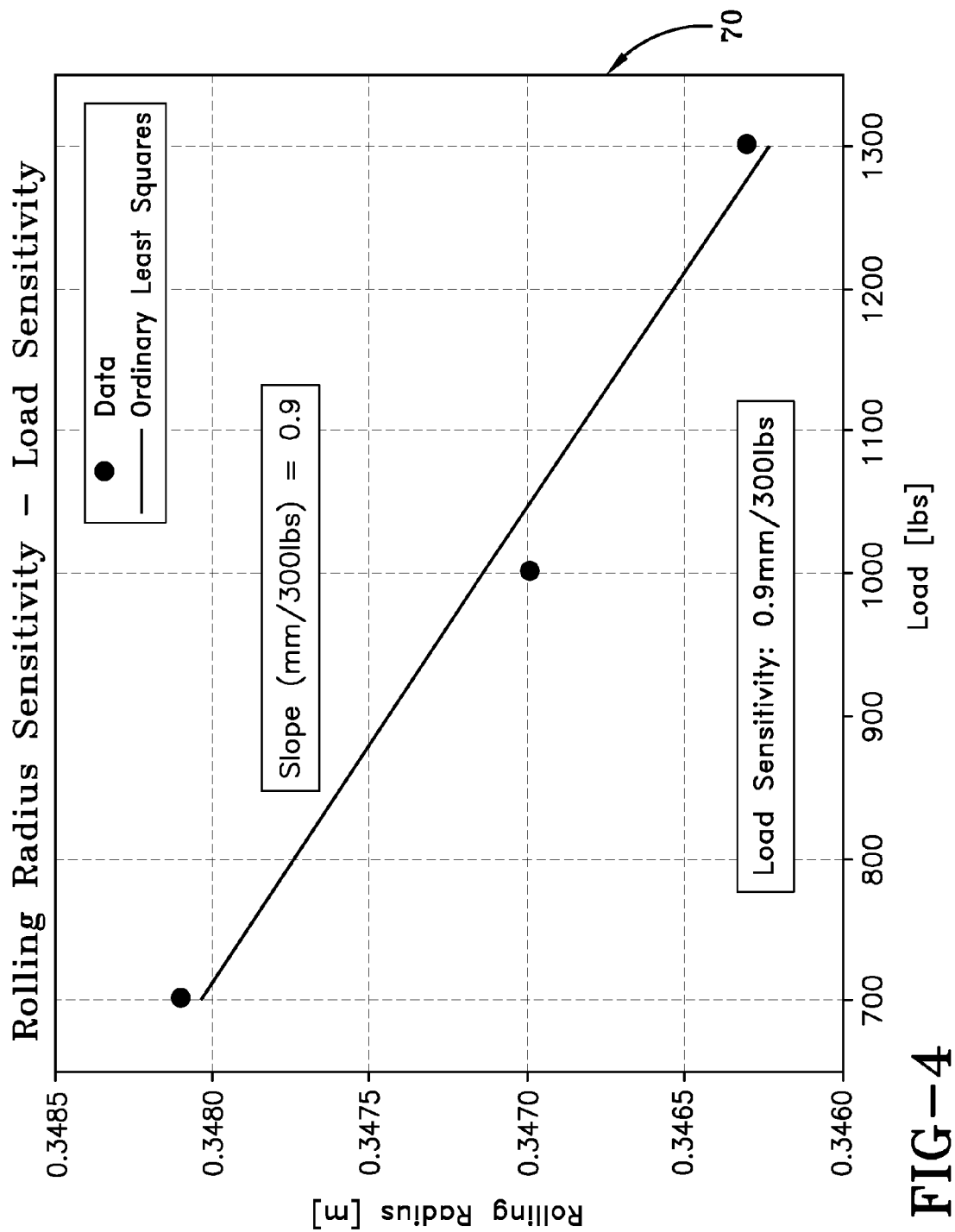
FIG. 4 is a load sensitivity graph showing how load affects rolling radius.

In FIG. 4, graph 70 shows data of rolling radius vs. tire loading in a straight line of ordinary least squares. The slope of the line of 0.9 mm/300 pounds is indicated. An inverse relationship is established and the noted sensitivity of rolling radius to load is thus indicated.

Figure 5:
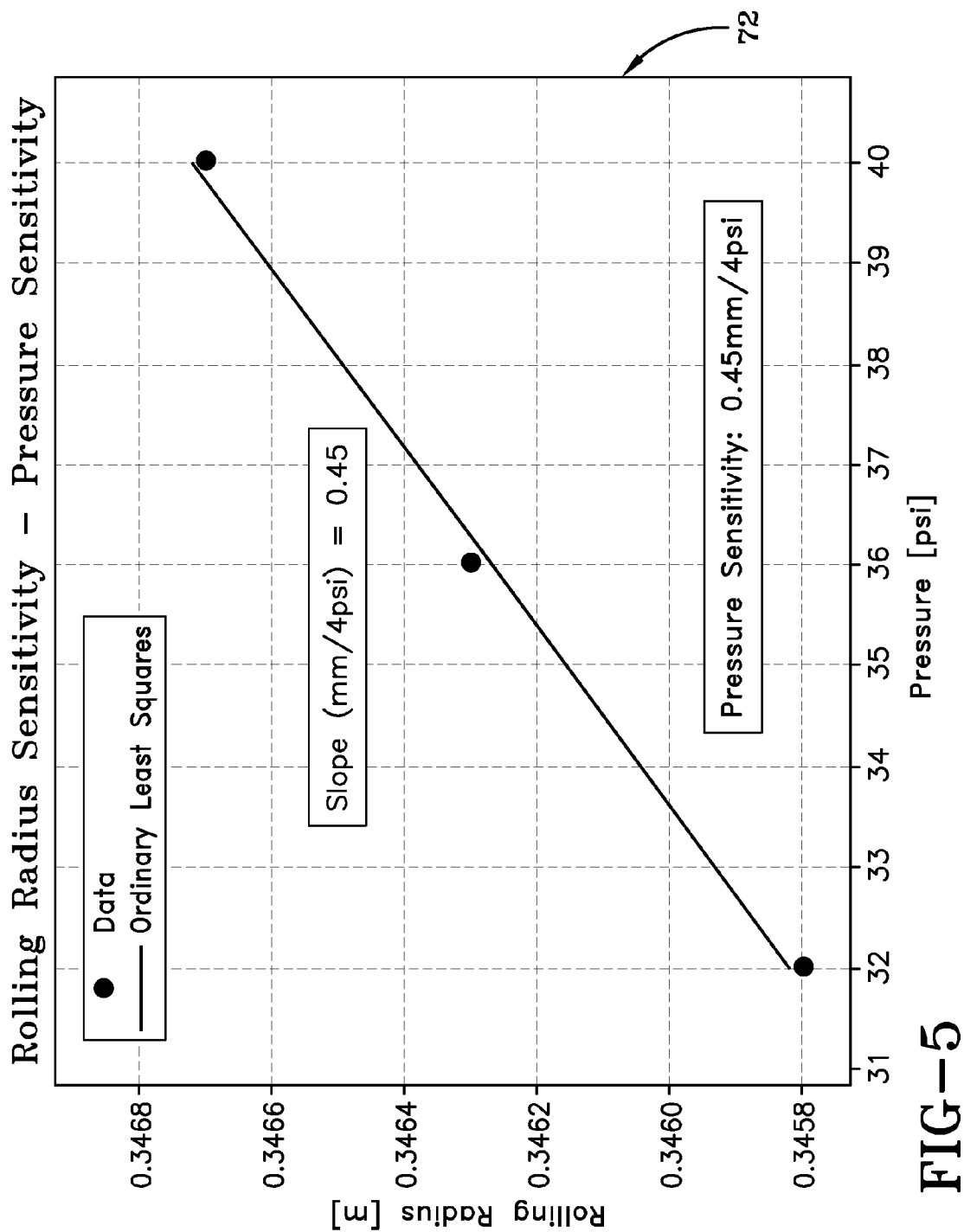
FIG. 5 is a pressure sensitivity graph showing how tire pressure affects rolling radius.

In FIG. 5, sensitivity of rolling radius to tire pressure is shown graphically at 72. A slope (mm/4 psi) of 0.45 is indicated showing that tire pressure has a significant impact on rolling radius of a tire. A positive relationship between pressure and rolling radius is seen.

Figure 6:
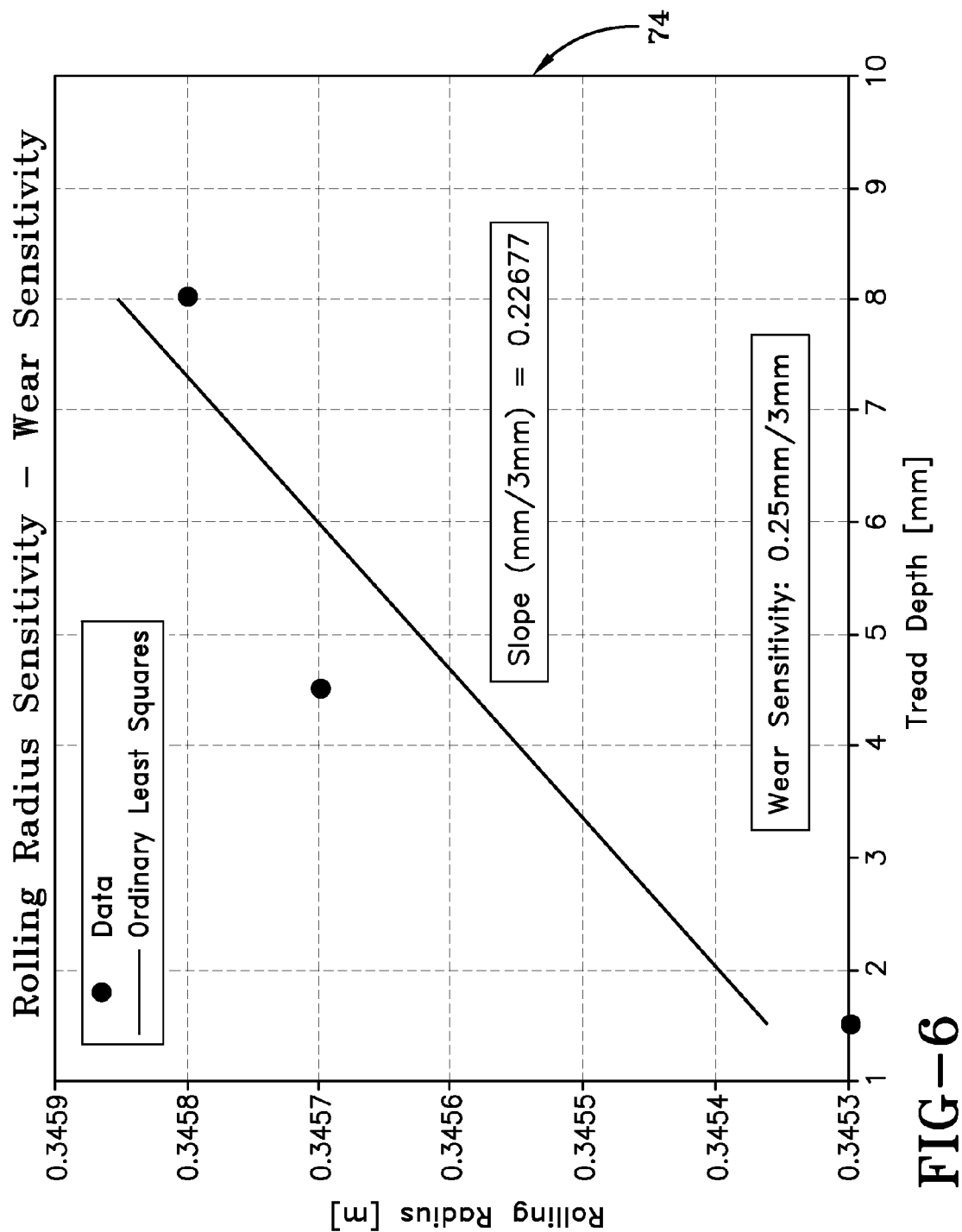
FIG. 6 is a wear sensitivity graph showing how tire wear affects rolling radius.

In FIG. 6, the sensitivity of rolling radius to tire wear state is shown graphically at 74, plotting rolling radius to tread depth [mm]. An inverse relationship at a slope (mm/3 mm) of 0.22677 is indicated.

The table 76 of FIG. 7 summarizes the sensitivities of rolling radius on tire operating conditions of load, pressure and tread depth. Increasing load decreases rolling radius, increasing pressure increases rolling radius and decreasing tread depth decreases rolling radius to the sensitivity indicated in column three. The system and methodology of FIG. 2 in compensating for the effect of tire load, pressure and tread depth is thus validated and quantified. From the relationship between load level, pressure and tire tread depth, knowing the tire ID, a compensation factor may be used at 48 by the compensator to compensate for the influence of these operating conditions. A more accurate rolling radius estimation 50 is thus made, resulting in a more accurate estimation 54 of vehicle speed. The vehicle speed 54, used in the determination of tire distance traveled, is accordingly rendered more accurate.

From the foregoing, a system and method for tracking tire mileage is achieved. Multiple tire-based sensors affixed to the tire generate tire-specific operating condition measurements such as tire ID, tire temperature and tire pressure. Tire wear state may be calculated based on such sensor inputs of tire operating conditions. Tire load state may further be determined using the TPMS provided tire operating condition measurements. The rolling radius estimation model 48 generates a tire rolling radius estimation compensated by the tire-specific operating condition measurements. From the rolling radius estimation 50, the vehicle speed estimator 54 generates a vehicle speed estimation from which vehicle speed 56 is determined and used to track the cumulative 58 mileage logged on the tire. The tire-affixed identification transponder generates a tire-specific identification code used in making the estimation of tire load and tire wear state tire-construction specific.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A tire tracking system for tracking travel mileage experienced by a vehicle tire comprising:
    a vehicle supported by at least one vehicle tire mounted to a wheel hub;
    a plurality of tire-based sensors affixed to the tire, wherein the tire-based sensors generate a plurality of tire-specific operating condition measurements, including a tire identification, a tire temperature and a tire pressure;
    a tire load estimator, the tire load estimator determining a tire load estimation from the tire-specific operating condition measurements;
    a tire pressure estimator, the tire pressure estimator determining the tire pressure from at least one of the tire-specific operating condition measurements;
    at least one vehicle-based sensor affixed to the vehicle, wherein the vehicle-based sensor generates at least one of a wheel speed and a hub acceleration measurement;
    a tire wear state estimator, the tire wear state estimator estimating a wear state of the tire from the at least one of a wheel speed and a hub acceleration measurement;
    a rolling radius estimation model that receives the tire load estimation, the tire pressure measurement and the tire wear state estimation and generates a compensated tire rolling radius a vehicle speed estimator that receives the compensated tire rolling radius and generates a vehicle speed estimation; and an aggregator that aggregates the vehicle speed estimation and yields a cumulative distance traveled for the tire.

2. The tire tracking system of claim 1, wherein the tire wear state estimator
receives the tire identification and estimates a tire-construction specific tire wear state estimate.

3. The tire tracking system of claim 1, wherein the tire load estimator
receives the tire identification and determines a tire-construction specific tire load estimate.

4. The tire tracking system of claim 1, wherein
the generated compensated rolling radius is adjusted based upon the inputs made for the particular tire construction indicated by the tire identification.

5. The tire tracking system of claim 1, wherein the at least one vehicle-based sensor is operative to generate a CAN-bus accessible wheel speed measurement for the tire.

6. The tire tracking system of claim 1, wherein the aggregator aggregates the vehicle speed estimation by at least one of time interval aggregation and integration.

7. A method for tracking travel mileage experienced by a vehicle tire comprising:
supporting a vehicle with at least one vehicle tire mounted to a wheel hub;
affixing a plurality of tire-based sensors to the tire, the tire-based sensors generating a plurality of tire-specific operating condition measurements, including a tire identification, a tire temperature and a tire pressure;
determining a tire load from the tire-specific operating condition measurements;
determining an estimated tire pressure from at least one of the tire-specific operating condition measurements;
affixing at least one vehicle-based sensor to the vehicle, the vehicle-based sensor generating at least one of a wheel speed and a hub acceleration measurement;
estimating a wear state of the tire from the at least one of a wheel speed and a hub acceleration measurement;
receiving the tire load estimation, the tire pressure measurement and the tire wear state estimation in a rolling radius estimation model and generating a compensated tire rolling radius;
receiving the compensated tire rolling radius in a vehicle speed estimator and generating a vehicle speed estimation; and
aggregating the vehicle speed estimation and yielding a cumulative distance traveled for the tire.

8. The method of claim 7, wherein
wherein the step of estimating a wear state of the tire includes receiving the tire identification and estimating a tire-construction specific tire wear state.

9. The method of claim 7, wherein
the step of determining a tire load includes receiving the tire identification and determining a tire-construction specific tire load estimate.

10. The method of claim 7, wherein
the step of generating a compensated tire rolling radius includes adjustments based upon the inputs made for the particular tire construction indicated by the tire identification.

11. The method of claim 7, wherein the step of affixing at least one vehicle-based sensor to the vehicle includes a sensor that is operative to generate a CAN-bus accessible wheel speed measurement for the tire.

12. The method of claim 7, wherein the step of aggregating the vehicle speed estimation includes aggregating the vehicle speed estimation by at least one of time interval aggregation and integration.

* * * * *